(12) United States Patent
Sawa et al.

(10) Patent No.: US 9,968,716 B2
(45) Date of Patent: May 15, 2018

(54) DRUG-ELUTING STENT GRAFT

(71) Applicants: Ono Pharmaceutical Co., Ltd., Osaka-shi (JP); Osaka University, Suita-shi (JP)

(72) Inventors: Yoshiki Sawa, Suita (JP); Toru Kuratani, Suita (JP); Koichi Toda, Suita (JP); Takayoshi Ueno, Suita (JP); Shigeru Miyagawa, Suita (JP); Satsuki Fukushima, Suita (JP); Atsuhiro Saito, Suita (JP); Yoshiki Watanabe, Suita (JP); Yoshiki Sakai, Suita (JP)

(73) Assignees: ONO PHARMACEUTICAL CO., LTD., Osaka (JP); OSAKA UNIVERSITY, Osaka (JP)

( * ) Notice: Subject to any disclaimer, the term of this patent is extended or adjusted under 35 U.S.C. 154(b) by 0 days. days.

(21) Appl. No.: 15/028,803

(22) PCT Filed: Sep. 10, 2014

(86) PCT No.: PCT/JP2014/073875
§ 371 (c)(1),
(2) Date: Apr. 12, 2016

(87) PCT Pub. No.: WO2015/056504
PCT Pub. Date: Apr. 23, 2015

(65) Prior Publication Data
US 2016/0250395 A1 Sep. 1, 2016

(30) Foreign Application Priority Data
Oct. 15, 2013 (JP) .................................. 2013-215067

(51) Int. Cl.
*A61L 31/16* (2006.01)
*A61F 2/07* (2013.01)
(Continued)

(52) U.S. Cl.
CPC ................ *A61L 31/16* (2013.01); *A61F 2/07* (2013.01); *A61F 2/82* (2013.01); *A61K 9/0024* (2013.01);
(Continued)

(58) Field of Classification Search
CPC ........ A61K 9/0024; A61K 47/34; A61K 47/36; A61K 47/42; A61K 31/343; A61F 2310/0097
See application file for complete search history.

(56) References Cited

U.S. PATENT DOCUMENTS

| 3,965,143 A | 6/1976 | Collins et al. |
| 4,132,738 A | 1/1979 | Kluender et al. |

(Continued)

FOREIGN PATENT DOCUMENTS

| CA | 2332375 A1 | 9/2000 |
| CA | 2332427 A1 | 9/2000 |

(Continued)

OTHER PUBLICATIONS

Masaki Kajimoto et al., "Basic fibroblast growth factor slow release stent graft for endovascular aortic aneurysm repair: A canine model experiment," Journal of Vascular Surgery, Nov. 2008, vol. 48, No. 5, pp. 1306-1314.
Sophie Lerouge et al., "Nitrogen-rich coatings for promoting healing around stent-grafts after endovascular aneurysm repair," Biomaterials, 2007; vol. 28 pp. 1209-1217.
J. M. Annemieke van der Bas et al., "Ingrowth of aorta wall into stent grafts impregnated with basic fibroblast growth factor: A porcine in vivo study of blood vessel prosthesis healing," Journal of Vascular Surgery, Apr. 2004, vol. 39, No. 4, pp. 850-858.
(Continued)

*Primary Examiner* — Jianfeng Song
(74) *Attorney, Agent, or Firm* — Locke Lord LLP

(57) ABSTRACT

The present invention provides a drug-eluting stent graft for preventing stent graft-related complications as well as treating aneurysm. Specifically, the present invention relates to a drug-eluting stent graft comprising a drug, a drug-retaining agent and a stent graft, and a method for therapy of aneurysm including the use of the drug-eluting stent graft.

17 Claims, 1 Drawing Sheet

(51) Int. Cl.
*A61L 31/14* (2006.01)
*A61F 2/82* (2013.01)
*A61K 47/34* (2017.01)
*A61K 47/36* (2006.01)
*A61K 47/42* (2017.01)
*A61K 31/343* (2006.01)
*A61K 31/4406* (2006.01)
*A61K 31/5585* (2006.01)
*A61K 9/00* (2006.01)

(52) U.S. Cl.
CPC ........ *A61K 31/343* (2013.01); *A61K 31/4406* (2013.01); *A61K 31/5585* (2013.01); *A61K 47/34* (2013.01); *A61K 47/36* (2013.01); *A61K 47/42* (2013.01); *A61L 31/148* (2013.01); *A61F 2240/001* (2013.01); *A61F 2250/0067* (2013.01); *A61F 2310/0097* (2013.01); *A61L 2300/412* (2013.01); *A61L 2300/602* (2013.01)

(56) References Cited

U.S. PATENT DOCUMENTS

| | | | |
|---|---|---|---|
| 5,234,457 A * | 8/1993 | Andersen | A61F 2/90 606/154 |
| 5,366,504 A | 11/1994 | Andersen et al. | |
| 5,405,378 A | 4/1995 | Strecker | |
| 5,462,968 A | 10/1995 | Woodward | |
| 5,480,998 A | 1/1996 | Hamanaka et al. | |
| 5,653,748 A | 8/1997 | Strecker | |
| 5,662,713 A | 9/1997 | Andersen et al. | |
| 5,674,276 A | 10/1997 | Andersen et al. | |
| 5,698,598 A | 12/1997 | Woodward | |
| 5,876,445 A | 3/1999 | Andersen et al. | |
| 6,019,785 A | 2/2000 | Strecker | |
| 6,046,233 A | 4/2000 | Kasukawa et al. | |
| 6,110,969 A | 8/2000 | Tani et al. | |
| 6,124,314 A | 9/2000 | Cameron et al. | |
| 6,146,416 A | 11/2000 | Andersen et al. | |
| 6,221,099 B1 | 4/2001 | Andersen et al. | |
| 6,235,780 B1 | 5/2001 | Ohuchida et al. | |
| 6,262,293 B1 | 7/2001 | Tani et al. | |
| 6,288,120 B1 | 9/2001 | Cameron et al. | |
| 6,305,436 B1 | 10/2001 | Andersen et al. | |
| 6,344,477 B1 | 2/2002 | Sharif | |
| 6,355,070 B1 | 3/2002 | Andersen et al. | |
| 6,376,502 B1 | 4/2002 | Cameron et al. | |
| 6,376,533 B1 | 4/2002 | Burk et al. | |
| 6,437,146 B1 | 8/2002 | Hattori et al. | |
| 6,462,080 B1 | 10/2002 | Klimko | |
| 6,462,081 B1 | 10/2002 | Maruyama et al. | |
| 6,476,074 B1 | 11/2002 | Stjernschantz et al. | |
| 6,485,515 B2 | 11/2002 | Strecker | |
| 6,492,412 B2 | 12/2002 | Cameron et al. | |
| 6,498,172 B1 | 12/2002 | Cameron et al. | |
| 6,505,654 B1 | 1/2003 | Andersen et al. | |
| 6,531,485 B2 | 3/2003 | Cameron et al. | |
| 6,545,045 B1 | 4/2003 | Klimko et al. | |
| 6,552,067 B2 | 4/2003 | Cameron et al. | |
| 6,562,868 B1 | 5/2003 | Stjernschantz et al. | |
| 6,576,785 B1 | 6/2003 | Tani et al. | |
| 6,586,462 B2 | 7/2003 | Burk et al. | |
| 6,610,719 B2 | 8/2003 | Paralkar et al. | |
| 6,642,266 B2 | 11/2003 | Cameron et al. | |
| 6,649,657 B2 | 11/2003 | Cameron et al. | |
| 6,737,437 B2 | 5/2004 | Cameron et al. | |
| 6,747,054 B2 | 6/2004 | Cameron et al. | |
| 6,861,441 B1 | 3/2005 | Clayton et al. | |
| 6,998,423 B2 | 2/2006 | Cameron et al. | |
| 7,166,631 B2 | 1/2007 | Congreve et al. | |
| 7,192,979 B2 | 3/2007 | Cameron et al. | |
| 7,205,302 B2 | 4/2007 | Asaki et al. | |
| 7,335,680 B2 | 2/2008 | Liao et al. | |
| 7,410,991 B2 | 8/2008 | Araldi et al. | |
| 7,442,702 B2 | 10/2008 | Cameron et al. | |
| 7,547,715 B2 | 6/2009 | Sakai et al. | |
| 7,635,713 B2 | 12/2009 | Liao et al. | |
| 7,699,886 B2 | 4/2010 | Sugimoto | |
| 7,732,622 B2 | 6/2010 | Congreve et al. | |
| 7,863,312 B2 | 1/2011 | Araldi et al. | |
| 8,058,305 B2 | 11/2011 | Liao et al. | |
| 8,436,026 B2 | 5/2013 | Sakai et al. | |
| 8,584,852 B2 | 11/2013 | Zucker | |
| 8,617,614 B2 | 12/2013 | Sakai et al. | |
| 8,642,630 B2 | 2/2014 | Sakai et al. | |
| 8,771,734 B2 | 7/2014 | Tabata | |
| 8,904,846 B2 | 12/2014 | Mader et al. | |
| 9,005,356 B2 | 4/2015 | Li et al. | |
| 2001/0006980 A1 | 7/2001 | Harada et al. | |
| 2001/0056060 A1 | 12/2001 | Cameron et al. | |
| 2002/0004495 A1 | 1/2002 | Harada et al. | |
| 2002/0035395 A1 * | 3/2002 | Sugimoto | A61F 2/91 623/1.15 |
| 2002/0044953 A1 | 4/2002 | Michelet et al. | |
| 2002/0065308 A1 | 5/2002 | Cameron et al. | |
| 2002/0115695 A1 | 8/2002 | Paralkar | |
| 2002/0161026 A1 | 10/2002 | Paralkar | |
| 2003/0083381 A1 | 5/2003 | Kumagai et al. | |
| 2004/0176423 A1 | 9/2004 | Paralkar | |
| 2006/0148691 A1 | 7/2006 | Tabata et al. | |
| 2007/0088068 A1 | 4/2007 | Congreve et al. | |
| 2008/0107703 A1 | 5/2008 | Tabata et al. | |
| 2008/0299089 A1 * | 12/2008 | Sakai | A61K 9/1647 424/93.7 |
| 2009/0324682 A1 * | 12/2009 | Popowski | A61K 9/0024 424/426 |
| 2010/0015196 A1 * | 1/2010 | Kimble | A61K 9/0024 424/423 |
| 2015/0151028 A1 | 6/2015 | Li et al. | |

FOREIGN PATENT DOCUMENTS

| | | |
|---|---|---|
| EP | 0860430 A2 | 8/1998 |
| EP | 0911321 A2 | 4/1999 |
| EP | 974580 A1 | 1/2000 |
| EP | 1080728 A1 | 3/2001 |
| EP | 1080729 A1 | 3/2001 |
| EP | 1110949 A1 | 6/2001 |
| EP | 1121939 A2 | 8/2001 |
| EP | 1132086 A2 | 9/2001 |
| JP | 07-500265 A | 1/1995 |
| JP | H07-41432 A | 2/1995 |
| JP | 2002-95756 A | 4/2002 |
| JP | 2002-104939 A | 4/2002 |
| JP | 2002-179595 A | 6/2002 |
| JP | 2004-115413 A | 4/2004 |
| JP | 2008-137975 A | 6/2008 |
| JP | 2008-532942 A | 8/2008 |
| JP | 4459543 B2 | 4/2010 |
| JP | 4685090 B2 | 5/2011 |
| JP | 2011-526163 A | 10/2011 |
| WO | WO-95/19964 A1 | 7/1995 |
| WO | WO-1996/026721 A1 | 9/1996 |
| WO | WO-98/28264 A1 | 7/1998 |
| WO | WO-98/58911 A2 | 12/1998 |
| WO | WO-99/02164 A1 | 1/1999 |
| WO | WO-99/19300 A1 | 4/1999 |
| WO | WO-99/33794 A1 | 7/1999 |
| WO | WO-00/03980 A1 | 1/2000 |
| WO | WO-00/16760 A2 | 3/2000 |
| WO | WO-00/18744 A1 | 4/2000 |
| WO | WO-00/21542 A1 | 4/2000 |
| WO | WO-00/38663 A2 | 7/2000 |
| WO | WO-00/38667 A2 | 7/2000 |
| WO | WO-00/38690 A2 | 7/2000 |
| WO | WO-00/40248 A1 | 7/2000 |
| WO | WO-00/54808 A1 | 9/2000 |
| WO | WO-00/54809 A1 | 9/2000 |
| WO | WO-01/10426 A2 | 2/2001 |
| WO | WO-01/72268 A1 | 10/2001 |
| WO | WO-02/42268 A2 | 5/2002 |
| WO | WO-02/47669 A1 | 6/2002 |
| WO | WO-02/064564 A1 | 8/2002 |

(56) References Cited

FOREIGN PATENT DOCUMENTS

| WO | WO-02/088084 A1 | 11/2002 |
|----|----|----|
| WO | WO-03/035064 A1 | 5/2003 |
| WO | WO-03/053923 A2 | 7/2003 |
| WO | WO-2004/032965 A1 | 4/2004 |
| WO | WO-2008/047863 A1 | 4/2008 |

OTHER PUBLICATIONS

Uri Pick, "Liposomes with a Large Trapping Capacity Prepared by Freezing and Thawing of Sonicated Phospholipid Mixtures," Archives of Biochemistry and Biophysics, Nov. 1981, vol. 212, No. 1, pp. 186-194.
Yasuhiko Tabata et al., "Protein release from gelatin matrices," Advanced Drug Delivery Reviews, 1998, vol. 31, pp. 287-301.
Yasuhiko Tabata, "Biomaterial technology for tissue engineering applications," J. R. Soc. Interface, 2009, vol. 6, pp. 311-324.
Masaya Yamamoto et al., "Controlled release of growth factors based on biodegradation of gelatin hydrogel," J. Biomater. Sci. Polymer. Edn., 2001, vol. 12, No. 1, pp. 77-88.
66th Annual Scientific Meeting of Japanese Association Thoracic Surgery on Oct. 2013 and English translation thereof.
International Search Report dated Dec. 16, 2014, issued for PCT/JP2014/073875.

* cited by examiner

[Fig. 1]
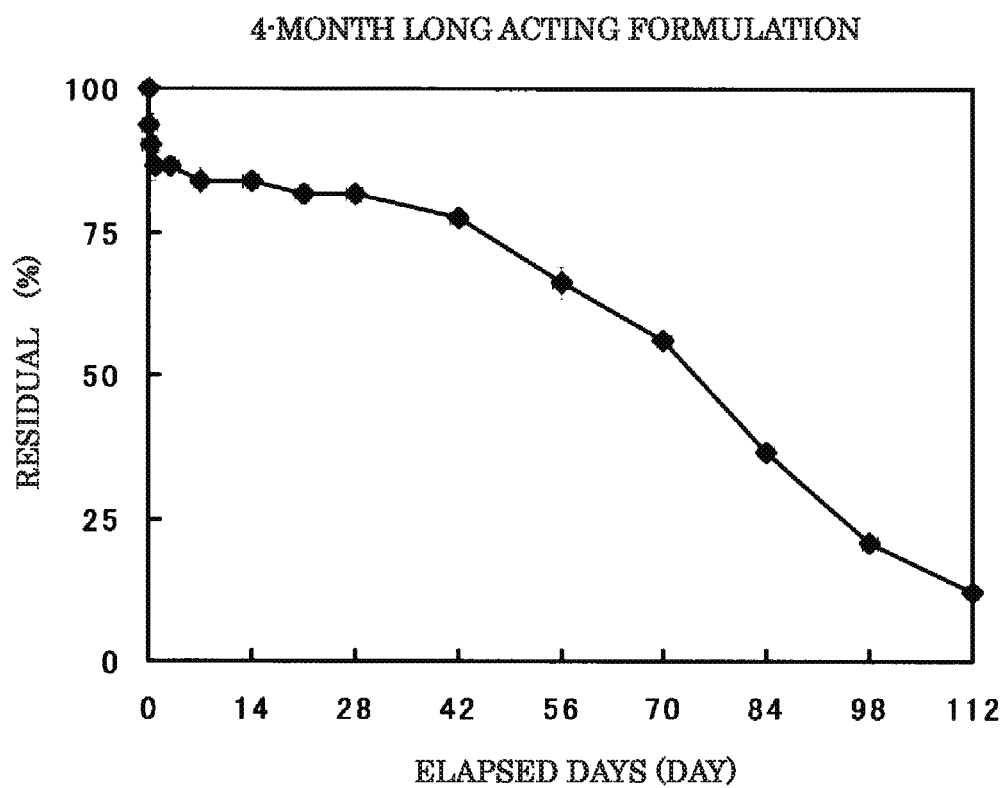
[Fig. 2]
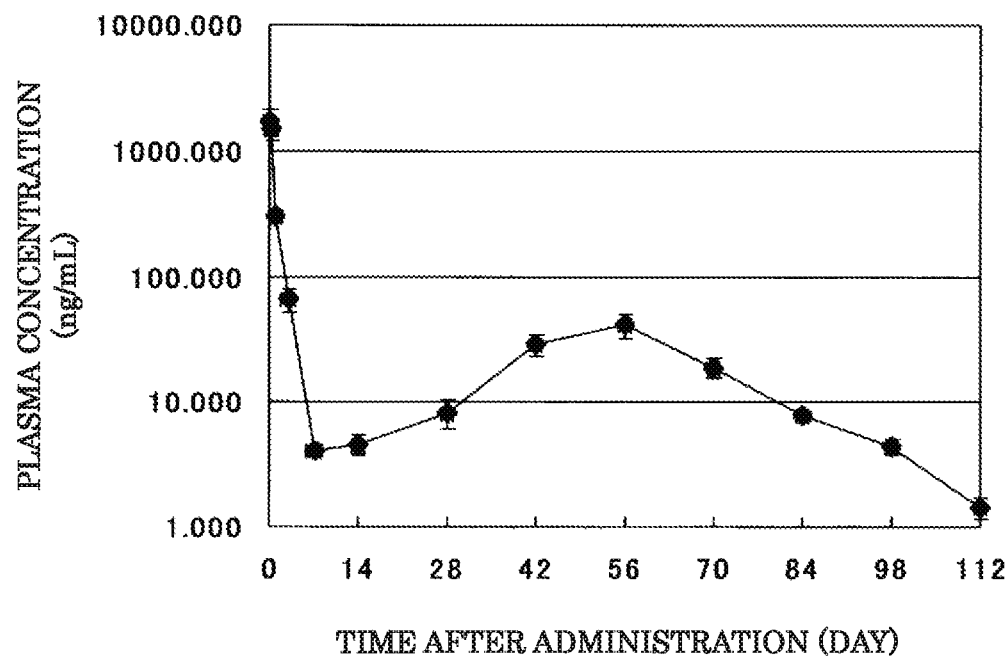

DRUG-ELUTING STENT GRAFT

TECHNICAL FIELD

The present invention relates to a novel drug-releasing stent graft for preventing stent graft-related complications after treatment of aortic aneurysm using stent grafts, a material or a method for preventing stent graft-related complications involving use of the stent graft and a material or a method for treating aneurysm involving use of the stent graft.

BACKGROUND ART

Aortic aneurysm is a recently increasing disease. One-fourth of aneurysms occur thoracically and three-fourth thereof occur abdominally. It is reported that 0.7 to 4.2% of the population are affected by the disease. Ruptured aneurysm has a mortality rate of 80 to 90%, which is very high, with the life-saving rate being 50% even when a trip to hospital by ambulance and surgery are successfully carried out. According to the Population Survey Report in Japan in 2012, aortic aneurysm, together with aortic dissection, is the 9th leading cause of death among females (7517 deaths/ 1.3%).

Cases of aneurysms having expanded diameters have been conventionally treated by blood vessel prosthesis implantation. Recently, however, a less invasive stent graft therapy replaces blood vessel prosthesis implantation and becomes rapidly prevalent. The principle and object of the therapy is to implant a stent graft at a relatively normal site of the vessel which is at a centre or periphery of an aortic aneurysm to block blood flow into the wall of the aortic aneurysm, thereby eliminating the pressure and preventing a fatal event such as aortic aneurysm rupture.

However, a huge issue of stent graft-related complications has been recognised even in large-scale clinical studies in Europe and the United States such as migration in which a stent graft is displaced from the implanted site late after implantation and endoleak in which blood flows into an aortic aneurysm through the gap between a stent graft and the vessel where the stent graft is implanted. According to the report from the Japanese Committee for Stentgraft Management, among 3124 cases of abdominal aortic aneurysm treated with stent grafts between 1 Jul. 2006 to 31 Dec. 2008, endoleak (16.8%) and migration (0.1%) were identified.

Preventing the stent graft-related complications is thus an urgent problem to be addressed. In order to solve the problem, research has been carried out to devise the methods including addition of basic fibroblast growth factor (bFGF) to a stent graft, as disclosed in the following Non Patent Literatures 1 to 3.

For example, a bFGF-releasing stent graft is reported in Non Patent Literature 1 that is prepared by impregnating a stent graft impregnated with collagen and heparin with a bFGF solution.

In Non Patent Literature 2, a bFGF-releasing stent graft is prepared by impregnating a stent graft with 10% water-soluble elastin and 0.5% heparin sodium salt followed by impregnation with 2 μg/mL bFGF solution.

In Non Patent Literature 3, a stent graft is prepared that is coated with an N-rich plasma-polymerised thin film (a thin ethylene film onto which a compound for promoting migration, adhesion and proliferation of cells comprising a high amount of nitrogen molecules such as amines, imines and nitriles is plasma-polymerised) serving as a scaffold for cells and promoting migration thereof.

However, none of the documents discloses an internal regenerating factor production-inducing agent, and HGF, VEGF, SDF-1, EGF, IGF-1, G-CSF and the like as an internal regenerating factor.

Meanwhile, Patent Literatures 1 and 2 disclose coating agents respectively comprising a stent or the like coated with an endogenous repair factor production-promoting agent such as $PGI_2$ (IP) agonist, $EP_2$ agonist and $EP_4$ agonist. However, the agents are for prevention of restenosis of, for example, the coronary artery and are not for prevention of stent graft-related complications (migration and endoleak) which are to be addressed by the present invention.

Therefore, the present invention is totally novel over the background art and is not suggested by the background art.

CITATION LIST

Patent Literature

[PTL 1] WO 2004/032965
[PTL 2] WO 2008/047863

Non Patent Literature

[NPL 1] Basic fibroblast growth factor slow release stent graft for endovascular aortic aneurysm repair: A canine model experiment (J Vasc Surg 2008; 48: 1306-14.)
[NPL 2] Nitrogen-rich coatings for promoting healing around stent-grafts after endovascular aneurysm repair (Biomaterials 28 (2007) 1209-1217)
[NPL 3] Ingrowth of aorta wall into stent grafts impregnated with basic fibroblast growth factor: A porcine in vivo study of blood vessel prosthesis healing (J Vasc Surg 2004; 39: 850-8.)

SUMMARY OF INVENTION

Technical Problem

An object of the present invention is to provide a drug-eluting stent graft which can prevent or reduce stent graft-related complications such as migration and endoleak resulting from insufficient fixation between stent grafts and the aorta. Specifically, an object of the present invention is to provide a drug-eluting stent graft that can provide early fixation to the aorta wall and prevent or reduce stent graft-related complications by applying, on the outside of a stent graft, a drug that promotes fixation to the aorta wall and allowing drug elution over a long period of time.

Another object of the present invention is to provide a method for preventing stent graft-related complications while treating aneurysms (thoracic aneurysms or abdominal aneurysms).

Solution to Problem

In order to solve the problem, the inventors of the present invention, while studying pharmacological actions of prostaglandins (PGs) which have similar actions to internal regenerating factors, focused on and studied the possibility of PGs inducing production of various internal regenerating factors.

As a result of the study, the inventors found that among PGs, agonists of IP receptor, $EP_2$ receptor and $EP_4$ receptor which promote production of cyclic AMP (cAMP) have an ability to promote tube formation in co-culture of normal human umbilical vein endothelial cells (HUVECs) and normal human dermal fibroblasts (NHDFs). As a result of further study, the inventors also found that the agonists can induce various internal regenerating factors from, for example, fibroblasts, smooth muscle cells, vascular endothelial cells and macrophages.

Specifically, for example, an internal regenerating factor production-inducing agent selected was a PGI biologically synthesised mainly in vascular endothelial cells and a selective IP receptor agonist (for example, Compound 1 disclosed in PTL 1: WO 2004/032965) which is an oxime (OX) derivative having a non-PG skeleton and has additionally an inhibitory activity on thromboxane (TX) $A_2$ synthase was selected. The inventors found that when Compound 1 was applied on the outside of a stent graft, production of various internal regenerating factors from surrounding cells could be promoted, mesenchymal stem cells (MSCs) from bone marrow cells could be induced locally at proximal to the stent graft to promote regeneration of tissue and fixation to autogenous tissue could be realised, thereby preventing or reducing stent graft-related complications.

Based on the above observations, the inventors carried out further studies to achieve the drug-eluting stent graft of the present invention.

Accordingly the present invention relates to the following:

Item 1. A drug-eluting stent graft comprising:
(a) a drug (excluding fibroblast growth factors (FGFs));
(b) a drug-retaining agent; and
(c) a stent graft, Item 2. The drug-eluting stent graft according to Item 1, wherein the stent graft (c) is coated with a mixture containing the drug (a) and the drug-retaining agent (b), Item 3. The drug-eluting stent graft according to Item 1 or 2, wherein the drug (a) comprises an internal regenerating factor production-inducing agent or an internal regenerating factor, Item 4. The drug-eluting stent graft according to any of Items 1 to 3, wherein the drug (a) is a slow-release formulation comprising an internal regenerating factor production-inducing agent or an internal regenerating factor, Item 5. The drug-eluting stent graft according to any of Items 1 to 4, wherein the drug (a) is a slow-release formulation comprising an internal regenerating factor production-inducing agent or an internal regenerating factor together with a biodegradable polymer, Item 6. The drug-eluting stent graft according to Item 4, wherein the drug (a) is a slow-release formulation comprising an internal regenerating factor production-inducing agent, Item 7. The drug-eluting stent graft according to Item 6, wherein the drug (a) is a microsphere formulation comprising an internal regenerating factor production-inducing agent, Item 8. The drug-eluting stent graft according to any of Items 5 to 7, wherein the drug (a) is a microsphere formulation comprising an internal regenerating factor production-inducing agent and a biodegradable polymer, Item 9. The drug-eluting stent graft according to any of Items 2 to 8, wherein the internal regenerating factor production-inducing agent is at least one selected from the group consisting of prostaglandin $I_2$ agonist, $EP_2$ agonist and $EP_4$ agonist, Item 10. The drug-eluting stent graft according to any of Items 2 to 9, wherein the internal regenerating factor production-inducing agent is prostaglandin $I_2$ agonist, Item 11. The drug-eluting stent graft according to Item 9 or 10, wherein the prostaglandin $I_2$ agonist is a compound represented by the following general formula (I):

[Chemical Formula 1]

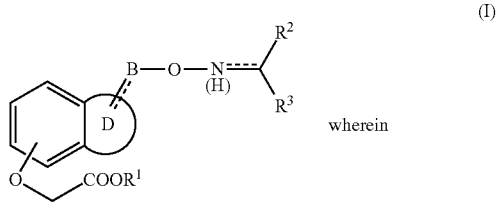

wherein

[Chemical Formula 2]

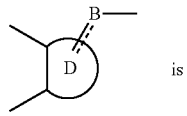

is

[Chemical Formula 3]

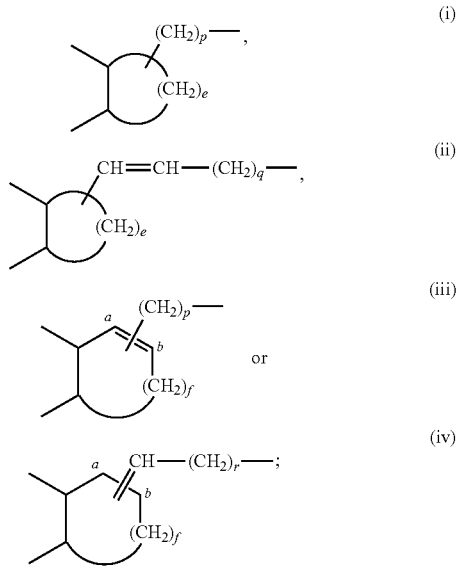

$R^1$ is a hydrogen atom or a C1-4 alkyl group;

$R^2$ is (i) a hydrogen atom, (ii) a C1-8 alkyl group which may be branched or form a ring, (iii) a phenyl group or a C4-7 cycloalkyl group, (iv) a 4- to 7-membered monocycle containing one nitrogen atom, (v) a C1-4 alkyl group substituted with a benzene ring or a C4-7 cycloalkyl group or (vi) a C1-4 alkyl group substituted with a 4- to 7-membered monocycle containing one nitrogen atom;

$R^3$ is (i) a C1-8 alkyl group which may be branched or form a ring, (ii) a phenyl group or a C4-7 cycloalkyl group, (iii) a 4- to 7-membered monocycle containing one nitrogen atom, (iv) a C1-4 alkyl group substituted with a benzene ring or a C4-7 cycloalkyl group, or (v) a C1-4 alkyl group substituted with a 4- to 7-membered monocycle containing one nitrogen atom;

e is an integer of 3 to 5; f is an integer of 1 to 3; p is an integer of 1 to 4; q is 1 or 2; and r is an integer of 1 to 3; and provided that when

[Chemical Formula 4]

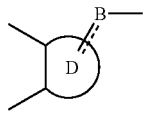

is the group represented by (iii) or (iv), —(CH$_2$)$_p$— and =CH—(CH$_2$)$_r$— are attached at the position a or b on the ring and the ring in R$^2$ and R$^3$ may be substituted with one to three C1-4 alkyl groups, C1-4 alkoxy groups, halogen atoms, nitro groups or trihalomethyl groups, or a salt thereof, Item 12. The drug-eluting stent graft according to Item 10 or 11, wherein the prostaglandin I$_2$ agonist is (E)-[5-[2-[1-phenyl-1-(3-pyridyl)methylidenaminoxy]ethyl]-7,8-dihydronaphthalen-1-yloxy]acetic acid or a salt thereof, Item 13. The drug-eluting stent graft according to Item 10, wherein the prostaglandin I$_2$ agonist is (±)-(1R,2R,3aS,8bS)-2,3,3a,8b-tetrahydro-2-hydroxy-1-[(E)-(3S, 4RS)-3-hydroxy-4-methyl-1-octen-6-ynyl]-1H-cyclopenta[b]-benzofuran-5-butanoic acid or a salt thereof, Item 14. The drug-eluting stent graft according to Item 6, wherein the drug (a) is a slow-release formulation comprising (E)-[5-[2-[1-phenyl-1-(3-pyridyl)methylidenaminoxy]ethyl]-7,8-dihydronaphthalen-1-yloxy]acetic acid or a salt thereof, Item 15. The drug-eluting stent graft according to Item 7, wherein the drug (a) is a microsphere formulation comprising (E)-[5-[2-[1-phenyl-1-(3-pyridyl)methylidenaminoxy]ethyl]-7,8-dihydronaphthalen-1-yloxy]acetic acid or a salt thereof, Item 16. The drug-eluting stent graft according to Item 5 or 8, wherein the biodegradable polymer is at least one selected from the group consisting of polylactic acid, polyglycolic acid, a lactic acid-glycolic acid copolymer, hydrogel and a mixture thereof, Item 17. The drug-eluting stent graft according to Item 7 or 8, wherein the microsphere formulation comprises (E)-[5-[2-[1-phenyl-1-(3-pyridyl)methylidenaminoxy]ethyl]-7,8-dihydronaphthalen-1-yloxy]acetic acid or a salt thereof and at least one biodegradable polymer selected from the group consisting of polylactic acid, polyglycolic acid, a lactic acid-glycolic acid copolymer, hydrogel and a mixture thereof, Item 18. The drug-eluting stent graft according to Item 16 or 17, wherein the biodegradable polymer has a weight average molecular weight of 6,000 to 50,000, Item 19. The drug-eluting stent graft according to any of Items 4 to 6, wherein the slow-release formulation is a microsphere formulation, Item 20. The drug-eluting stent graft according to Item 19, wherein the microsphere formulation contains an internal regenerating factor production-inducing agent or an internal regenerating factor at 5 to 30% by weight, Item 21. The drug-eluting stent graft according to Item 19 or 20, wherein the microsphere formulation has an average particle diameter of 15 to 50 μm, Item 22. The drug-eluting stent graft according to any of Items 1 to 21, wherein the drug-retaining agent (b) is a bioabsorbable polymer, Item 23. The drug-eluting stent graft according to Item 22, wherein the bioabsorbable polymer is at least one selected from the group consisting of fibrin, gelatin, collagen and hyaluronic acid, Item 24. The drug-eluting stent graft according to Item 23, wherein the bioabsorbable polymer is at least one selected from the group consisting of fibrin, atelocollagen and gelatin, Item 25. The drug-eluting stent graft according to any of Items 1 to 24, wherein the stent graft includes a mixture comprising gelatin and a microsphere formulation containing (E)-[5-[2-[1-phenyl-1-(3-pyridyl)methylidenaminoxy]ethyl]-7,8-dihydronaphthalen-1-yloxy]acetic acid, the mixture being applied on the outside of the stent graft.

Item 26. The drug-eluting stent graft according to any of Items 1 to 25, which is used to be placed at an aneurysmal portion in a mammal, Item 27. The drug-eluting stent graft according to any of Items 1 to 26, which is used to prevent a stent graft-related complication, Item 28. The drug-eluting stent graft according to Item 27, wherein the stent graft-related complication is migration and/or endoleak, Item 29. A method for preparing a drug-eluting stent graft, comprising coating a stent graft (c) with a mixture containing a drug (a) (excluding fibroblast growth factors (FGFs)) and a drug-retaining agent (b), Item 30. A method for treating aneurysm, comprising placing the drug-eluting stent graft according to any of Items 1 to 28 at an aneurysmal portion, Item 31. A material for treatment of aneurysm, comprising the drug-eluting stent graft according to any of Items 1 to 28, Item 32. A method for preventing of a stent graft-related complication, comprising placing the drug-eluting stent graft according to any of Items 1 to 28 at an aneurysmal portion, and Item 33. A material for prevention of a stent graft-related complication, comprising the drug-eluting stent graft according to any of Items 1 to 28.

Advantageous Effects of Invention

The drug-eluting stent graft of the present invention includes an agent applied thereon that promotes fixation of a stent graft to the aorta, and thus can promote tissue repair and effectively prevent or reduce stent graft-related complications (such as migration and endoleak). Moreover, by using the drug-eluting stent graft of the present invention, development of stent graft-related complications can be suppressed while effectively treating aneurysms (thoracic aneurysms and abdominal aneurysms) in mammals.

BRIEF DESCRIPTION OF DRAWINGS

FIG. 1 shows the result of release (profile of residual rate over time) of the active ingredient from the microsphere formulation produced in Formulation Example 1; and FIG. 2 shows blood kinetics of the active ingredient in the microsphere formulation produced in Formulation Example 1.

DESCRIPTION OF EMBODIMENTS

A drug-eluting stent graft of the present invention is characterised in that it includes (a) a drug (excluding fibroblast growth factors (FGFs)), (b) a drug-retaining agent and (c) a stent graft.

(a) Drug

As used herein, the term "drug (excluding fibroblast growth factors (FGFs))" is not particularly limited as far as it is a drug excluding FGFs. This term encompasses any pharmaceutical materials which are systemically or locally administered in an oral or parenteral form.

Specific examples of the drug include internal regenerating factor proteins, internal regenerating factor-producing genes, internal regenerating factor production-inducing agents, low-molecular compounds, proteins, polypeptides, polynucleotides, antisense, decoy, antibodies, extracellular matrix, cell adhesion factors, vaccine, stem cells isolated from tissue, iPS cells, somatic cells and the like. Examples of low-molecular compounds include antithrombotic agents, circulation improving agents, smooth muscle relaxants, vasodilators, anti-inflammatory agents, local anaesthetics, analgesics, metabolism improving agents and prostaglandins. The "drug" in the present invention may be one or a combination of two or more of these pharmaceutical materials.

In an embodiment of the "drug", an internal regenerating factor production-inducing agent or an internal regenerating factor (excluding FGFs) may be mentioned. The internal regenerating factor production-inducing agent or the internal regenerating factor is preferably in the form of a slow-release formulation.

Examples of the internal regenerating factor (excluding FGFs) include vascular endothelial growth factor (VEGF), hepatocyte growth factor (HGF), transforming growth factor-β (TGF-β), platelet-derived growth factor (PDGF), angiopoietin, hypoxia-inducible factor (HIF), insulin-like growth factor (IGF), bone morphogenetic protein (BMP), connective tissue growth factor (CTGF), epidermal growth factor (EGF), nerve growth factor (NGF), brain-derived neurotrophic factor (BDNF), glial cell line-derived neurotrophic factor (GDNF), stem cell factor (SCF), stromal cell-derived factor (SDF-1), granulocyte colony-stimulating factor (G-CSF), keratinocyte growth factor (KGF), chondrocyte growth factor (CGF), leukemia inhibitory factor (LIF) and Kruppel-like transcription factor (KLF) and the like and growth factors belonging to the same families as the foregoing. Extracellular matrix (such as fibronectins, laminins and proteoglycans) and cell adhesion factor (such as cadherins and integrins) are also encompassed.

Examples of the internal regenerating factor production-inducing agent include an agent comprising one or more selected from prostaglandin (PG) $I_2$ agonists, $EP_2$ agonists and $EP_4$ agonists.

Examples of $PGI_2$ agonist include $PGE_1$ and $PGI_2$ derivatives thereof (e.g. 6-oxo-$PGE_1$, ornoprostil, limaprost, enprostil and misoprostol), prodrugs thereof and sustained-release formulations thereof (e.g. lipo-$PGE_1$). $EP_2$ and $EP_4$ agonists include various PGE derivatives, prodrugs thereof and sustained-release formulations (slow-release formulations) thereof.

Other examples of the internal regenerating factor production-inducing agent include Cholera toxin, 8-bromo-cAMP, dibutyryl-cAMP, Forskolin, AT1 receptor blockers (ARBs), peroxysome proliferator-activated receptor gamma (PPARγ) agonists, HMG-CoA reductase inhibitors, phosphodiesterase (PDE) inhibitors, IL-1, TNF-α, INF and the like.

Examples of ARBs include losartan, candesartan, valsartan, telmisartan and the like, examples of PDE inhibitors include theophyline, milrinone, tadalafil, dipyridamole, sildenafil and the like, examples of HMG-CoA reductase inhibitors include atorvastatin, simvastatin, pravastatin and the like, and examples of PPARγ agonists include thiazolidine derivatives such as pioglitazone, rosiglitazone and the like.

When the internal regenerating factor is a protein, the internal regenerating factor may be a peptide corresponding to an active site of the protein and the internal regenerating factor production-inducing agent may be a gene encoding the corresponding protein.

$PGI_2$ agonist (IP receptor agonist) encompasses both $PGI_2$ agonists which have been known to date and $PGI_2$ agonists which will be discovered in future.

For example, $PGI_2$ agonist is preferably a compound represented by the general formula (I) or a salt thereof.

General Formula (I):

[Chemical Formula 5]

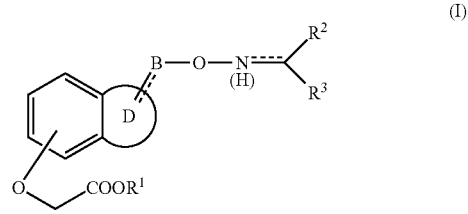

In the general formula (I):

[Chemical Formula 6]

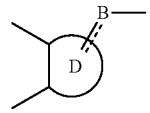

is preferably

[Chemical Formula 7]

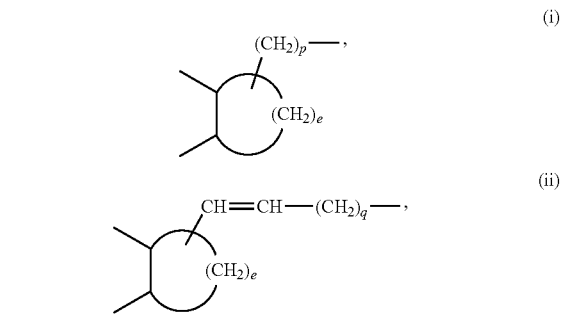

-continued

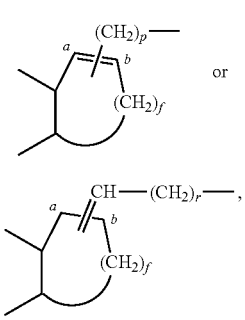

and more preferably

[Chemical Formula 8]

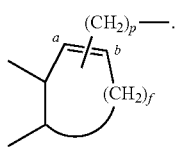

In the general formula (I), $R^2$ is preferably:
(iii) a phenyl group or a C4-7 cycloalkyl group;
(iv) a 4- to 7-membered monocycle containing one nitrogen atom;
(v) a C1-4 alkyl group substituted with a benzene ring or a C4-7 cycloalkyl group; or
(vi) a C1-4 alkyl group substituted with a 4- to 7-membered monocycle containing one nitrogen atom;
and more preferably:
(iii) a phenyl group or a C4-7 cycloalkyl group; or
(iv) a 4- to 7-membered monocycle containing one nitrogen atom.

In the general formula (I), $R^3$ is preferably:
(ii) a phenyl group or a C4-7 cycloalkyl group;
(iii) a 4- to 7-membered monocycle containing one nitrogen atom;
(iv) a C1-4 alkyl group substituted with a benzene ring or a C4-7 cycloalkyl group; or
(v) a C1-4 alkyl group substituted with a 4- to 7-membered monocycle containing one nitrogen atom;
and more preferably:
(ii) a phenyl group or a C4-7 cycloalkyl group; or
(iii) a 4- to 7-membered monocycle containing one nitrogen atom.

In the general formula (I), e is an integer of 3 to 5; f is an integer of 1 to 3; p is an integer of 1 to 4; q is 1 or 2; and r is an integer of 1 to 3; provided that when

[Chemical Formula 9]

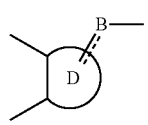

is the group represented by (iii) or (iv), —$(CH_2)_p$— and =CH—$(CH_2)_r$— are attached at the position a or b on the ring and further provided that the ring in $R^2$ and $R^3$ may be substituted with one to three C1-4 alkyl groups, C1-4 alkoxy groups, halogen atoms, nitro groups or trihalomethyl groups.

A salt of the compound represented by the general formula (I) is not particularly limited as far as it is a pharmaceutically acceptable salt. Examples thereof include a sodium salt and a potassium salt, among which a sodium salt is preferred.

More preferable compounds represented by the general formula (I) or a salt thereof include the following compounds (oxime derivatives).

Compound 1: (E)-[5-[2-[1-phenyl-1-(3-pyridyl)methylidenaminoxy]ethyl]-7,8-dihydronaphthalen-1-yloxy]acetic acid

[Chemical Formula 10]

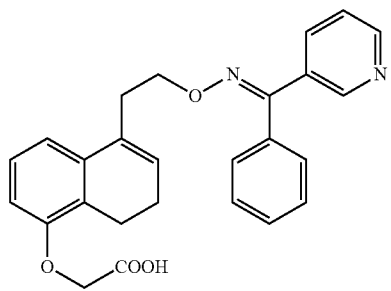

Compound 2: (Z)-[5-[2-[1-phenyl-1-(3-pyridyl)methylidenaminoxy]ethyl]-7,8-dihydronaphthalen-1-yloxy]acetic acid

[Chemical Formula 11]

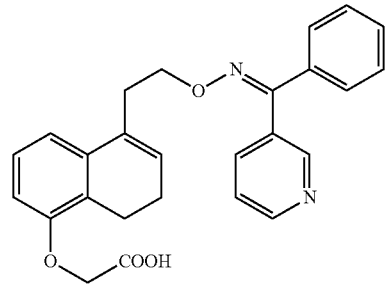

Other examples of $PGI_2$ agonists include:
Beraprost sodium (Compound 3): ((±)-(1R,2R,3aS,8bS)-2,3,3a,8b-tetrahydro-2-hydroxy-1-[(E)-(3S,4RS)-3-hydroxy-4-methyl-1-octen-6-ynyl]-1H-cyclopenta[b]benzofuran-5-butanoic acid sodium salt);
OP-2507 (Compound 4): (5-{(3aR,4R,6aS)-5-hydroxy-4-[(1E,3S)-3-hydroxy-3-(cis-4-propylcyclohexyl)prop-1-enyl]-3,3a,4,5,6,6a-hexahydrocyclopenta[b]pyrrol-2-yl}pentanoic acid methyl ester);
MRE-269 (Compound 5): 2-{4-[N-(5,6-diphenylpyrazin-2-yl)-N-isopropylamino]butyloxy}-acetic acid;
Compound 6 (NS-304), which is a derivative of Compound 5: 2-{4-[N-(5,6-diphenylpyrazin-2-yl)-N-isopropylamino]butyloxy}-N-(methylsulphonyl)acetamide;
Ornoprostil (Compound 7), which is a $PGE_1$ derivative: (17S,20-dimethyl-6-oxo-prostaglandin $E_1$ methyl ester); and Limaprost, which is a PGE$_1$ derivative: ((E)-7-{(1R,2R,3R)-3-hydroxy-2-[(3S,5S)-E-3-hydroxy-5-methyl-1-nonenyl]-5-oxocyclopentyl}-2-heptenoic acid); and carbacyclin derivatives which are PGI$_2$ derivatives.

Among the compounds represented by the general formula (I) or pharmaceutically acceptable salts thereof, Compound 1 which is chemically stable is preferable for preparation of a slow-release formulation. Compound 3 or Compound 5 is also preferred.

It is disclosed in U.S. Pat. No. 5,480,998 that Compound 1 or a salt thereof, which is used as a PGI$_2$ agonist (IP receptor agonist) in the present invention and is an oxime (OX) derivative represented by the general formula (I) above, has platelet aggregation inhibitory activity, platelet adhesion inhibitory activity, vasodilation activity and gastric secretion inhibitory activity, and thus is useful for prevention and/or treatment of thrombosis, arteriosclerosis, ischemic heart disease, gastric ulcer, hypertension and the like.

WO 2004/032965 and WO 2008/047863 disclose the treatment of various damages to cells or organs by angiogenesis, the induction of differentiation of various stems cells, anti-apoptosis and anti-fibrogenesis based on the induction of production of internal regenerating factors.

Among the PGI$_2$ agonists used in the present invention, for example, a preparation method for the compounds represented by the general formula (I) is disclosed in U.S. Pat. No. 5,480,998.

For example, Compound 1: (E)-[5-[2-[1-phenyl-1-(3-pyridyl)methylidenaminoxy]ethyl]-7,8-dihydronaphthalen-1-yloxy]acetic acid is described in Example 2 (g) of U.S. Pat. No. 5,480,998.

The preparation method for beraprost sodium (Compound 3): ((±)-(1R,2R,3aS,8bS)-2,3,3a,8b-tetrahydro-2-hydroxy-1-[(E)-(3S,4RS)-3-hydroxy-4-methyl-1-octen-6-ynyl]-1H-cyclopenta[b]benzo furan-5-butanoic acid, sodium salt) is disclosed in WO 1996/026721.

The preparation method for MRE-269 (Compound 5): 2-{4-[N-(5,6-diphenylpyrazin-2-yl)-N-isopropylamino]butyloxy}acetic acid and the derivative thereof (NS-304; Compound 6) is disclosed in WO 02/088084.

In the present invention, the above-mentioned pharmaceutical compounds may be used respectively alone or in combination of two or more.

As used herein, PGI$_2$ agonist (IP receptor agonist) encompasses both PGI$_2$ agonists which have been known to date and PGI$_2$ agonists which will be discovered in future.

EP$_2$ agonist encompasses both EP$_2$ agonists which have been known to date and EP$_2$ agonists which will be discovered in future. Preferable EP$_2$ agonists include compounds described in European Patent Specification No. 0860430, U.S. Pat. No. 6,110,969, WO 99/33794, European Patent Specification No. 974580, WO 95/19964, WO 98/28264, WO 99/19300, European Patent Specification No. 0911321, WO 98/58911, U.S. Pat. No. 5,698,598, U.S. Pat. No. 6,376,533, U.S. Pat. No. 4,132,738 and U.S. Pat. No. 3,965,143. Particularly preferably EP$_2$ agonist is (5Z,9β,11α,13E)-17,17-propano-11,16-dihydroxy-9-chloro-20-nor-prosta-5,13-dienoic acid and salts thereof.

EP$_4$ agonist encompasses both EP$_4$ agonists which have been known to date and EP$_4$ agonists which will be discovered in future. Preferable EP$_4$ agonists include compounds described in WO 00/03980, WO 99/02164, WO 00/16760, WO 00/18744, WO 00/21542, WO 00/38663, WO 00/38690, WO 00/38667, WO 00/40248, WO 00/54808, WO 00/54809, WO 01/10426, European Patent Specification No. 1110949, European Patent Specification No. 1121939, European Patent Specification No. 1132086, WO 200172268, Japanese Patent Application Laid-open No. 2002-104939, WO 02/42268, Japanese Patent Application Laid-open No. 2002-179595, WO 02/47669, WO 02/64564, WO 03/035064, WO 03/053923 and U.S. Pat. No. 6,552,067. Particularly preferably EP$_4$ agonist is (11α,13E,15α)-9-oxo-11,15-dihydroxy-16-(3-methoxymethylphenyl)-17,18,19,20-tetranor-5-thiaprost-13-enoic acid and esters thereof.

In the present invention, it was investigated to complete prompt fixation to the aorta wall by allowing a stent graft to contain an internal regenerating factor production-inducing agent or an internal regenerating factor on the outer surface thereof to allow sustained release of the agent or factor during angiogenesis (regeneration) and tissue repair.

As candidates of the internal regenerating factor production-inducing agent or the internal regenerating factor, attention was paid to, for example, compounds represented by the general formula (I) (particularly Compound 1) or Compound 3 or Compound 5 which have, in addition to vasodilation ability of vessels with ischemic regions and an ability to increase blood flow in inhibition of platelet aggregation, an ability to continuously induce production of various internal regenerating factors in the vicinity of damaged sites. By allowing a stent graft to contain the compound on the outer surface thereof, partial fixation of the stent graft to the aorta wall was possible. However, fixation of the stent graft to the aorta wall was not always perfect because the compound was not continuously released due to an initial burst. Thus, in order to allow prompt fixation of the stent graft placed in an aneurysm to the aorta wall, it was necessary to configure a sustained-release formulation which releases the compound during angiogenesis (regeneration) and tissue repair.

Thus it was concluded that in the present invention it is preferable not only to allow the stent graft to contain the internal regenerating factor production-inducing agent or the internal regenerating factor on the outer surface thereof but also to configure the agent or the factor in the form of a slow-release formulation.

Slow-release formulations of various internal regenerating factor production-inducing agents and internal regenerating factors and preparing methods thereof are disclosed in, for example, WO 2004/032965 and WO 2008/047863 in details.

In the present invention, the slow-release formulation is not particularly limited as far as it can continuously provide the active ingredient from the outer surface of the stent graft placed in an aneurysm. Examples thereof include slow-release injections (such as microcapsule formulations, microsphere formulations and nanosphere formulations), implantable formulations (such as film formulations, fibres, patches and meshes), ointments, coating agents in which the active ingredient is contained or coated in or on the medical devices (such as stents, fixation screws and sutures), and the like.

Amicrocapsule formulation, microsphere formulation and nanosphere formulation of the present invention is a pharmaceutical composition in the form of fine particles that includes an effective component (internal regenerating factor production-inducing agent or internal regenerating factor) as active ingredient, and is made of a bioabsorbable polymer or a biodegradable polymer.

Examples of a bioabsorbable polymer used for the slow-release formulation include natural polymers and synthetic polymers. The mechanism of controlling the release rate from the formulation may be any of decomposition control, diffusion control and film penetration control, and the like.

Examples of natural polymers as the bioabsorbable polymer include plant-produced polysaccharides (such as cellulose, starch and alginic acid), animal-produced polysaccharides and proteins (such as chitin, chitosan, collagen, gelatin, gelatin hydrogel, albumin, glycosaminoglycan and fibrin), microorganism-produced polyesters and polysaccharides (such as poly-3-hydroxyalkanoate and hyaluronic acid) and the like.

Examples of the biodegradable polymer include a polymer and copolymer of fatty acid ester, polyacrylate ester, poly(hydroxybutyrate), poly(alkylene oxalate), poly(orthoester), polycarbonate and poly(amino acid), which may be used alone or in combination of two or more. Examples of the polymer and copolymer of fatty acid ester include polylactic acid, polyglycolic acid, polycitric acid, polymalic acid, polyethylene succinate, polybutylene succinate, poly (ε-caprolactone), poly(butylene terephthalate-adipate) and a lactic acid-glycolic acid copolymer, which may be used alone or in combination of two or more.

Alternatively, poly(α-cyanoacrylate), poly(β-hydroxybutyrate), poly(trimethylene oxide), poly(orthoester), poly(orthocarbonate), poly(ethylene carbonate), poly(γ-benzyl-L-glutamate), polyvinyl alcohol, polyester carbonate, polyacid anhydride, polycyanoacrylate, polyphosphazene or poly(L-alanine) may be used alone or a mixture of two or more of the foregoing may be used.

Gelatin hydrogel, polylactic acid, polyglycolic acid, a lactic acid-glycolic acid copolymer or a mixture thereof is preferred, and polylactic acid or a lactic acid-glycolic acid copolymer is more preferred.

The weight average molecular weight of the biodegradable polymer is not limited and is preferably about 2,000 to about 800,000 and more preferably about 5,000 to about 200,000. For example, polylactic acid preferably has a weight average molecular weight of about 5,000 to about 100,000 and more preferably about 6,000 to about 50,000. Polylactic acid can be prepared according to any method well known per se. A lactic acid-glycolic acid copolymer preferably has a composition ratio of lactic acid and glycolic acid of about 100/0 to about 50/50 (W/W) and particularly preferably about 90/10 to 50/50 (W/W). A lactic acid-glycolic acid copolymer preferably has a weight average molecular weight of about 5,000 to about 100,000 and more preferably about 10,000 to about 80,000. A lactic acid-glycolic acid copolymer can be prepared according to any method well known per se. A basic amino acid (such as alginic acid) and the like may be added in order to prevent initial burst.

The weight average molecular weight refers to the molecular weight measured by gel permeation chromatography (GPC) with reference to polystyrene standard.

The slow-release formulation of the present invention is preferably a microsphere formulation. The microsphere formulation generally contains a drug (particularly an internal regenerating factor production-inducing agent or an internal regenerating factor) at 5 to 30% by weight, preferably at 10 to 25% by weight and more preferably at 10 to 20% by weight. The microsphere formulation generally has an average particle diameter of 15 to 50 μm, preferably 20 to 50 μm and more preferably 20 to 40 μm. The average particle diameter used herein is measured on a laser diffraction particle size analyser (such as SALD-2100 (Shimadzu Corporation)) and a Coulter counter (produced by Beckman Coulter, Multisizer 3) which are in general use.

A slow-release microsphere (MS) formulation or a slow-release nanosphere (NS) formulation, containing as a drug, an internal regenerating factor production-inducing agent including compounds represented by the general formula (I) (particularly Compound 1), a protein formulation of an internal regenerating factor or a peptide formulation containing an active site thereof can be prepared by using gelatin hydrogel (Japanese Patent Application Laid-open No. 2004-115413, Japanese Patent No. 4459543, Japanese Patent No. 4685090, Japanese Patent Application Laid-open No. 2008-137975, etc.), by using liposome or lipid (Japanese Patent Application Laid-open No. H07-41432, Arch. Biochem. Biophys., 212, 186, 1981, etc.) and the like, without using the above biodegradable polymer.

Gelatin hydrogel is hydrogel obtained from gelatin by chemically crosslinking various chemical crosslinking agents and gelatin molecules. Examples of the chemical crosslinking agent include glutaraldehyde, water-soluble carbodiimide such as EDC, a condensation agent forming chemical bonds between, for example, propylene oxides, diepoxy compounds, hydroxy groups, carboxyl groups, amino groups, thiol groups, imidazole groups and the like. Glutaraldehyde is preferred. Gelatin can alternatively be chemically crosslinked by heat treatment or ultraviolet irradiation. The crosslinking treatments may be used in combination. Hydrogel can also be prepared by physical crosslinking utilizing salt bridge, electrostatic interaction, hydrogen bonding, hydrophobic interaction and the like.

The average particle diameter of the resulting gelatin hydrogel particles varies depending on the concentration of gelatin, the volume ratio between gelatin aqueous solution and olive oil and stirring speed during preparation of the particles. Generally, the average particle diameter is 1 to 1000 μm. Particles having a desired diameter according to the purpose may be obtained by sifting.

A MS formulation of drug-impregnated gelatin hydrogel can be obtained by adding a buffer containing a drug to gelatin hydrogel to allow penetration of the drug into gelatin hydrogel.

By this method, a slow-release formulation containing bioabsorbable polymer hydrogel and a growth factor, cytokine, monokine, lymphokine, other physiologically active substances and the like can be prepared (Adv. Drug Deliv. Rev., 31, 287-301, 1998, J. R. Soc. Interface, 6 Suppl. 3, S311-S324, 2009, J. Biomater. Sci. Polym. Edn., 12, 77-88, 2001).

For example, when a drug is trapped into gelatin hydrogel, the drug is hardly released from hydrogel. However, when hydrogel is decomposed in vivo, gelatin molecules become water-soluble and the drug trapped into the gelatin molecules can be released. Namely, the release rate of the drug can be controlled by decomposition of hydrogel. Decomposition of hydrogel can be varied by adjusting the degree of crosslinking during preparation of hydrogel. In addition, because of the interaction of the drug with gelatin, stability, including resistance to enzymatic degradation, of the drug in vivo is also increased.

A liposome formulation refers to cell-like fine particles which are artificial nanospheres made of phospholipids or glycolipids constituting biological membranes and having a particle diameter of about 100 nm. A liposome formulation containing a water-soluble or lipophilic drug can be used as a slow-release formulation.

Examples of phospholipids used include a glycerophospholipid selected from phosphatidylcholine, phosphatidylethanolamine, phosphatidylserine, phosphatidic acid, phosphatidylglycerol, phosphatidylinositol, cardiolipin, egg yolk lecithin, hydrogenated egg yolk lecithin, soy lecithin and hydrogenated soy lecithin; a sphingophospholipid selected from sphingomyelin, ceramide phsophorylethanolamine and ceramide phosphorylglycerol; and a plasmalogen. Examples of glycolipids include a glycerolipid selected from digalactosyl diglyceride and a sulphate ester of galactosyl diglyceride; a sphingoglycolipid selected from galactosylceramide, a sulphate ester of galactosylceramide, lactosylceramide, ganglioside G7, ganglioside G6 and ganglioside G4.

The amount of the bioabsorbable polymer or the biodegradable polymer used may be varied as far as the purpose of the present invention is fulfilled according to the strength of pharmacological activity of the drug and desired drug release. The amount is, for example, about 0.2 to 10,000 times (mass ratio) of the drug, preferably about 1 to 1,000 times (mass ratio) and still more preferably about 1 to 100 times (mass ratio) of the drug.

The microspheres, microcapsules, nanocapsules and nanospheres of the present invention can be prepared by, for example, in-water drying (such as o/w method, w/o method and w/o/w method), phase separation method, spray drying method, formation method of particles with supercritical fluid and methods according to the foregoing.

Specifically, the compound represented by the general formula (I) (particularly Compound 1) is, due to the structural characteristics thereof, preferably included in a microsphere (MS) formulation (Compound 1 MS) containing a lactic acid-glycolic acid copolymer (PLGA) or polylactic acid (PLA). Compound 1 MS is designed to be hydrolysed into lactic acid and glycolic acid at the site of administration and almost linearly release Compound 1 into the body. By changing the molecular weight of PLGA, the lactic acid/glycolic acid ratio, particle diameter and the like, a slow-release formulation over 1 week to 6 months can be prepared (WO 2008/047863).

Compound 1 is a low-molecular oxime (OX) derivative having a non-PG skeleton and has TX $A_2$ synthase inhibitory activity as well as selective IP agonistic action. Compound 1 can further induce various internal regenerating factors such as hepatocyte growth factor (HGF), vascular endothelial growth factor (VEGF), epidermal growth factor (EGF), insulin-like growth factor (IGF-1), stromal cell-derived factor (SDF-1) and granulocyte colony-stimulating factor (G-CSF) in co-culture with NHDFs and HUVECs. An ability to promote production of endogenous $PGI_2$ and $PGE_2$ is also confirmed.

Compound 1 is the most suitable drug in the present invention because, due to induction of various internal regenerating factors, effects of anti-apoptosis, promotion of angiogenesis, induction of differentiation of stem cells and anti-fibrogenesis are expected.

(b) Drug-Retaining Agent

In the present invention, a drug-retaining agent is used in order to retain a drug (excluding FGFs) at a stent graft. Although the drug can be continuously released by formulating the drug in a slow-release formulation as described above, a desired effect may not be obtained when the drug per se is detached from the stent graft due to blood flow and the like. Thus by firmly retaining the drug on the stent graft with the drug-retaining agent, the effect of the slow-release formulation can be more effectively exhibited.

The drug-retaining agent is not particularly limited as far as it can retain an internal regenerating factor production-inducing agent or internal regenerating factor and/or a slow-release formulation (microsphere formulation, nanosphere formulation, etc.) including the agent or factor onto a stent graft, and is preferably a bioabsorbable polymer or a biodegradable polymer and more preferably a bioabsorbable polymer.

Examples of the bioabsorbable polymer include natural polymers and synthetic polymers.

Examples of natural polymers include plant-produced polysaccharides (such as cellulose, starch and alginic acid), animal-produced polysaccharides and proteins (such as chitin, chitosan, collagen, gelatin, gelatin hydrogel, albumin and glycosaminoglycan), microorganism-produced polyesters and polysaccharides (such as poly-3-hydroxyalkanoate and hyaluronic acid) and the like. Among these, fibrin, gelatin, collagen and hyaluronic acid are preferred and fibrin, atelocollagen and gelatin are more preferred.

Examples of the biodegradable polymer include a polymer and copolymer of fatty acid ester, polyacrylate ester, poly(hydroxybutyrate), poly(alkylene oxalate), poly(orthoester), polycarbonate and poly(amino acid), which may be used alone or in combination of two or more. Examples of the polymer and copolymer of fatty acid ester include polylactic acid, polyglycolic acid, polycitric acid, polymalic acid, polyethylene succinate, polybutylene succinate, poly (ε-caprolactone), poly(butylene terephthalate-adipate) and a lactic acid-glycolic acid copolymer, which may be used alone or in combination of two or more. Alternatively, poly(α-cyanoacrylate), poly(β-hydroxybutyrate), poly(trimethylene oxide), poly(orthoester), poly(orthocarbonate), poly(ethylene carbonate), poly(γ-benzyl-L-glutamate), polyvinyl alcohol, polyester carbonate, polyacid anhydride, polycyanoacrylate, polyphosphazene or poly(L-alanine) may be used alone or a mixture of two or more of the foregoing may be used. Gelatin hydrogel, polylactic acid, polyglycolic acid or a lactic acid-glycolic acid copolymer is preferred, and a lactic acid-glycolic acid copolymer is more preferred.

The weight average molecular weight of the biodegradable polymer is not particularly limited and is preferably about 2,000 to about 800,000 and more preferably about 5,000 to about 200,000.

The drug-retaining agent of the present invention may be added with an additive, if necessary, according to the purpose. Examples of the additive include a dispersant, a preservative, an antioxidant and the like.

In the present invention, a drug-retaining agent and a drug are mixed to be ready, for example, to coat or to be applied on the outside of a stent graft. For example, a drug-retaining agent may be impregnated with a drug and moulded in a desired shape (film, sheet, etc.) or a suspension or a solution containing a drug-retaining agent and a drug with optionally a solvent may be prepared and made into a spray or an adhesive agent. The obtained mixture of a drug-retaining agent and a drug such as the film, the sheet, the spray, the adhesive agent is used to coat a stent graft to obtain a drug-eluting stent graft of the present invention. Thereby the drug can be continuously released at the outside of the stent graft. It is of course preferable that the drug is in the form of a sustained-release formulation.

(c) Stent Graft

The stent graft used for the present invention is an artificial blood vessel used for intravascular surgery such as for aneurysm, and is a metal wire mesh tube coated inside and/or outside thereof with a resin.

The resin may be a thermoplastic resin. Examples of the thermoplastic resin include a polyolefin such as polyethylene, polypropylene, ethylene-α-olefin copolymers, a polyamide, a polyurethane, a polyester such as polyethylene terephthalate, polybutylene terephthalate, polycyclohexane terephthalate and polyethylene-2,6-naphthalate, a fluororesin such as PTFE and ETFE and the like. Fluororesins such as PTFE and ETFE which are chemically stable, have high durability and have low tissue reaction, and polyesters such as polyethylene terephthalate which are chemically stable, have high durability, have low tissue reaction and have excellent mechanical properties such as tensile strength are more preferred. Polyesters such as polyethylene terephthalate having a glass transition temperature of 60° C. or higher are particularly preferred because a polyester resin may have a decreased strength due to body temperature. Alternatively a material which is soluble in vivo such as PET/PGA, PGA/PLLA, PLGA and PDS may be used.

The resin is preferably in the form of fabric. The fabric is preferably a twill fabric, a plain woven fabric or a knitted fabric of a resin and may be in the form of a velour. A twill fabric and a plain woven fabric are preferred because a large fabric having low wall thickness and high tensile strength can be easily prepared. The fabric has any thickness without limitation. However, the thickness is preferably in the range of 10 to 160 μm, more preferably 10 to 95 μm and particularly preferably 20 to 95 μm.

The stent graft is designed for every patient so that the stent graft fits the affected site of the patient.

Examples of the stent graft include Gore TAG® (produced by Gore, U.S.), VALIANT® (Produced by Medtronic, U.S.A.), Relay Plus® (Produced by Bolton Medical, Spain) and Zenith TX2® (produced by Cook Medical, U.S.A.) for thoracic aortic aneurysms and EXCLUDER® (produced by Gore, U.S.A.), Zenith® (produced by Cook Medical, U.S.A.), Endurant® (produced by Medtronic, U.S.A.) and Powerlink (Endologix, Inc., U.S.A.) for abdominal aortic aneurysms, all of which are already pharmaceutically approved in Japan.

The drug-eluting stent graft of the present invention is obtained by coating the outside (the side that contacts the intra-arterial wall) of the stent graft with a mixture containing the drug (excluding FGFs) and the drug-retaining agent. By placing the stent graft at the affected aneurysm site in a mammal, development of stent graft-related complications can be prevented while effectively treating aneurysms (thoracic aneurysm and abdominal aneurysm).

EXAMPLES

Specific embodiments of the present invention are described hereafter. The embodiments are for better understanding of the present invention and do not limit the scope of the invention.

Formulation Example 1 (Production of Sustained-Release Microsphere Formulation)

A sustained-release microsphere (MS) formulation was produced according to the following procedures.

A biodegradable polymer PLA0020 (1 g, composition: DL-lactic acid 100%, weight average molecular weight: 20,000, intrinsic viscosity: 0.177 to 0.216 dl/g, Wako Pure Chemical Industries, Ltd.) and 250 mg of (E)-[5-[2-[1-phenyl-1-(3-pyridyl)methylidenaminoxy]ethyl]-7,8-dihydronaphthalen-1-yloxy]acetic acid (Compound 1 disclosed in U.S. Pat. No. 5,480,998) were suspended in 10 mL of $CH_2Cl_2$ and dissolved by adding 2 mL of methanol.

The solution was added to 1.5 L of 0.1% (w/v) PVA solution (adjusted to pH 7 with phosphoric acid) with stirring at 5,000 rpm in Physcotron (homogenizer type NS-60, generator shaft type NS-20, Nition Medical and Physical Instruments) at the vicinity of the side of the impeller using a pipette to obtain an o/w emulsion. The o/w emulsion was stirred at room temperature for about 4 hours to evaporate $CH_2Cl_2$ and methanol and solidify the oil phase.

The oil phase was centrifuged (3,000 rpm, 10 minutes) on a centrifuge (himac CR5B2, Hitachi Koki Co., Ltd.) to remove a supernatant, dispersed in purified water (50 mL) and then centrifuged (3,000 rpm, 10 minutes). The supernatant was removed and the precipitate was dispersed in 0.2% (w/v) Tween 80 solution (30 mL) and centrifuged (3,000 rpm, 10 minutes). The supernatant was then removed, the precipitate was again dispersed in purified water (30 mL), centrifuged (3,000 rpm, 10 minutes) and the supernatant was removed. The precipitate was frozen in dry ice-methanol and dried under reduced pressure (about 12 hours) to obtain a MS formulation.

The resulting MS formulation had an encapsulation efficiency of Compound 1 of 70% or higher, had a content of Compound 1 of 17.9% and had an average particle diameter of 25.8 μm.

<Measurement of Encapsulation Efficiency and Content>

To the MS formulation (about 10 mg) prepared in Formulation Example 1, an appropriate amount of an acetonitrile solution containing an internal standard was added and dissolved by ultrasonication. The amount of Compound 1 in the thus prepared solutions was measured by high performance liquid chromatograph (HPLC) and the encapsulation efficiency and content of Compound 1 in the MS formulation were calculated by the following equations:

Encapsulation efficiency (%)=(Measured amount of Compound 1/Theoretical amount of Compound 1)×100

Content (%)=(Measured amount of Compound 1/Amount of microsphere)×100

<Particle Diameter Measurement>

The average particle diameter of the MS formulation was measured on a Coulter counter (Multisizer III, Beckman Coulter Inc., USA).

Formulation Example 2 (Production of Control Microsphere Formulation)

A MS formulation was prepared in the same manner as in Formulation Example 1 except that Compound 1 (250 mg) was not added. A control MS formulation without Compound 1 was thus obtained. The MS formulation had an average particle diameter of 25.8 μm.

Test Example 1 (In Vitro Release Test)

The MS formulation prepared in Formulation Example 1 was weighed (3 mg) for each sampling point (n=3), added with 10 mL of 1/15 M phosphate buffer, pH 7, containing 0.2 (w/v) % Tween 80, homogeneously dispersed by voltexing (10 seconds) and ultrasonication (20 seconds) and left to stand in a thermostatic bath at 37° C. Samples in containers were removed from the bath over time and centrifuged (2,000 rpm, 5 minutes), and 4 mL of the supernatant and a pellet after removing the rest of the supernatant were frozen and stored.

To the pellet, 10 mL of DMSO was added and voltexed (10 seconds) to thoroughly dissolve the MS formulation. To this solution (300 μL), 200 μL of internal standard solution (IS solution) and 500 μL of mobile phase (pH 3) were added and thoroughly mixed. Similarly, to 300 μL of the supernatant 200 μL of IS solution and 500 μL of mobile phase (pH 3) were added and thoroughly mixed. After centrifugation (12,000 rpm, 3 minutes), 10 μL of the supernatant was injected to HPLC.

<HPLC Conditions>

Instrument: chromatograph (Shimadzu LC-10AT), UV detector (Shimadzu SPD-10A), data analyser (Shimadzu C-R7A)

Detection: UV-265 nm

Column: SHISEIDO CAPCELLPACK C18 UG120 (4.6 mm i.d×150 mm)

Column temperature: constant temperature at around 25° C.

Mobile phase: acetonitrile:water:triethylamine=1000:900:3 (a solution of water:triethylamine=900:3 was adjusted to pH 3 with phosphoric acid)

Flow rate: 1.0 mL/min

<Preparation of Internal Standard Solution (IS Solution)>

Internal standard (IS): n-propylparaben (100 mg) was weighed and diluted with ethanol to 100 mL. This solution (10 mL) was diluted with ethanol to 100 mL. This solution (10 mL) was diluted with ethanol to 100 mL to obtain the IS solution.

The result of release of the MS formulation prepared in Formulation Example 1 is shown in FIG. 1. As shown in FIG. 1, the microsphere formulation of Formulation Example 1 released 90% or more Compound 1 over about 4 months.

Test Example 2 (In Vivo Release Test)

Blood kinetics were analysed using male SD rats (SPF, Japan SLC, Inc.). Rats were administered at the back with a single subcutaneous injection of a suspension at the amount corresponding to 10 mg of Compound 1 (Formulation Examples 1 and 2)/kg using a 23G disposable needle (Terumo Corporation) and a 2.5-mL disposable syringe (Terumo Corporation). The dose was 5 mL/kg. Each group contained 5 animals.

At each blood collection time, 0.5 mL of blood was collected via the jugular vein using a disposable syringe with a 23G needle to which heparin was attached and centrifuged (12,000 rpm, 10 minutes, 4° C.), and plasma was frozen (−30° C.) and stored. After the test, the blood concentration of Compound 1 was measured by LC/MS/MS.

<LC/MS/MS Analysis>

MS/MS conditions;

MS/MS: API 4000

Ionisation mode: ESI

Ion polarity mode: positive

TABLE 1

| Compound | Monitored ions: | |
|---|---|---|
| | Precursor ion* (m/z) | Product ion* (m/z) |
| Compound 1 | 429.2 | 79.2 |
| Internal standard (IS) | 445.4 | 168.1 |

*The highest ionic strength is arbitrarily selected within m/z ± 0.5 from a target value.

Blood kinetics of the MS formulation of Formulation Example 1 are shown in FIG. 2. According to FIG. 2, the MS formulation showed blood kinetics of about 4 months.

Example 1 (Production of Drug-Eluting Stent Graft)

Gelatin (1 g, product name: MediGelatin, type: HMG-BP, manufacturer and distributor: Nippi, Inc.) was dissolved in 10 mL of saline. To the solution (0.5 mL), 100 mg of the MS formulation of Formulation Example 1 or the same amount of the MS formulation of Formulation Example 2 was suspended to prepare Suspension 1 or Suspension 2, respectively.

Stent grafts (SG) (25 mm length/14 to 18 mm diameter) each formed with a stainless steel Z stent (product name: Gianturco Z stent, type: 30 mm, manufacturer and distributor: Cook Medical) and a woven polyester graft (product name: J Graft Woven-Graft, type: WST series 14, 16, 18 mm, distributor: Japan Lifeline Co., Ltd., manufacturer: UBE Junken Medical) were prepared, Suspension 1 or Suspension 2 was applied on the outside of each stent graft and dried for solidification to prepare Stent graft 1 or Stent graft 2.

Example 2 (Histological Analysis and Mechanical Tensile Test)

To female HBD dogs each weighing 20 kg (purchased from Oriental Yeast Co., Ltd.), Stent graft 1 or Stent graft 2 was inserted under general anaesthesia to the thoracic descending aorta via the abdominal aorta by retroperitoneal approach. After 1, 2 or 3 months, animals (N=4 each) were dissected and subjected to histological analysis and mechanical tensile test (product name and type: Tensilon RTC-1150A, company: Orientec Co.).

The blood concentration of Compound 1 after insertion of Stent graft 1 is shown in Table 2. The concentration was highest immediately after administration (7.21±1.90 ng/dl) and it was demonstrated that the drug release was maintained even after 2 months (0.57±0.57 ng/dl).

TABLE 2

| | Blood concentration (ng/mL) | | | | | | | | |
|---|---|---|---|---|---|---|---|---|---|
| | Immediately after surgery | 1 day | 3 days | 1 week | 2 weeks | 3 weeks | 1 month | 2 months | 3 months |
| Average | 7.21 | 1.08 | 0.37 | 0.25 | 0.16 | 0.23 | 0.48 | 0.57 | 0.14 |
| ±S.D. | 1.90 | 0.98 | 0.25 | 0.20 | 0.08 | 0.11 | 0.39 | 0.57 | 0.13 |

After insertion of Stent graft 1, the concentration of Compound 1 in the vascular tissue at the stent graft region was measured (Table 3). It was demonstrated that even after 3 months, Compound 1 remained in the vascular tissue. For histological adhesion of the stent graft to the aorta wall, migration of cells into the graft and histological integration with the aorta wall in situ by proliferation of extracellular matrix (ECM) such as collagen fibres are required.

TABLE 3

Concentration in vascular tissue (ng/wet g)

|  | 1 month | 2 months | 3 months |
|---|---|---|---|
| Average | 21725 | 1690.8 | 35.25 |
| ±S.D. | 12962.3 | 1995.6 | 25.13 |

In sections stained with HE, the number (A) of nuclei in the graft and the area (B) of the graft were measured. On the basis of the definition: cell density in the graft=A/B ($\times 10^3/\mu m^2$), the number of cells (α-SMA positive cells; smooth muscle cells) in the graft was calculated, of which result is shown in Table 4. The number of cells in the graft was increased with Formulation Example 1 compared to Formulation Example 2.

TABLE 4

Cell count test in graft ($\times 10^3/\mu m^2$)

|  | 1 month | | 2 months | | 3 months | |
|---|---|---|---|---|---|---|
|  | Formulation Example 1 | Formulation Example 2 | Formulation Example 1 | Formulation Example 2 | Formulation Example 1 | Formulation Example 2 |
| Average | 16.79 | 13.26 | 22.34 | 11.68 | 22.11 | 12.41 |
| ±S.D. | 7.77 | 4.38 | 8.90 | 5.51 | 6.35 | 3.85 |

In histological analysis, proliferation of CD31 positive cells (aortic endothelial cells) on the surface of the neointima and α-SMA positive cells (aortic smooth muscle cells) in the layer below the surface were observed, and further preferable tissue regeneration was observed over time. In sections stained by Masson trichrome staining, the area of the regions stained blue (fibrotic regions: A) and that of the regions excluding the white regions (whole tissue: B) were respectively measured in the tissue between the graft and the aorta on Biorevo BZ-9000 (Keyence) and the rate of fibrogenesis was calculated on the basis of the definition: rate of fibrogenesis=A/B (%). As a result, as shown in Table 5, fibrogenesis was significantly promoted with Formulation Example 1.

TABLE 5

Fibrogenesis test between graft and aorta (%)

|  | 1 month | | 2 months | | 3 months | |
|---|---|---|---|---|---|---|
|  | Formulation Example 1 | Formulation Example 2 | Formulation Example 1 | Formulation Example 2 | Formulation Example 1 | Formulation Example 2 |
| Average | 47.66 | 40.74 | 66.52 | 62.01 | 75.35 | 66.09 |
| ±S.D. | 13.27 | 10.24 | 13.65 | 13.52 | 8.55 | 13.10 |

In the mechanical tensile test, a section of the aorta wall and the graft and aorta wall tissue in the shape of a strip of 5×10 mm was attached to the arms of Tensilon RTC-1150A via mosquito clamps, tensile force was applied to the strip at a rate of 50 mm/min and the maximum load at which the graft was detached from the aorta wall tissue was measured. As a result, as shown in Table 6, the maximum load required for detachment was increased by 1.17 times (P=0.025) at 2 months and 1.17 times (P=0.014) at 3 months for Formulation Example 1, indicating an increase in the fixation strength.

TABLE 6

Tensile Test (N)

|  | 1 month | | 2 months | | 3 months | |
|---|---|---|---|---|---|---|
|  | Formulation Example 1 | Formulation Example 2 | Formulation Example 1 | Formulation Example 2 | Formulation Example 1 | Formulation Example 2 |
| Average | 2.350 | 2.007 | 5.429 | 4.636 | 6.269 | 5.367 |
| ±S.D. | 1.001 | 0.678 | 1.259 | 1.121 | 0.834 | 0.767 |

From the above results, when the drug-eluting stent graft which slowly releases Compound 1 was placed in the aorta, regeneration of tissues between the stent graft and the aorta wall was promoted and fixation was improved. It was found that the drug-eluting stent graft can avoid complications due to insufficient fixation between the stent graft and the aorta.

Example 3 (Promotion of cAMP Production by Compound 1 in In Vitro Normal Human Aortic Smooth Muscle Cell (AoSMC) Culture)

Cells (produceed by Lonza, purchased from Takara Bio Inc., product name: normal human aortic smooth muscle cells (AoSMCs), product code: CC-2571) were cultured in a medium (produced by Lonza, purchased from Takara Bio Inc., product name: smooth muscle cell medium kit-2 (5% FBS), SmGM™-2 Bullet Kit™, product code: CC-3182) for 72 hours. To the culture medium at the number of cells of $4.0\times10^5$ cells which was rendered to be serum free, Compound 1 dissolved in DMSO was added so as to be 100 nM or 1000 nM. As a control, the same amount of DMSO was added to the culture medium. After 72 hours of culture, the supernatant was recovered and cAMP in the culture medium was measured with the cAMP EIA kit Code. 581001.

The result is shown in Table 7. From the result, it was found that Compound 1 increased production of cAMP in normal human aortic smooth muscle cells (AoSMCs).

TABLE 7

Promotion of cAMP production by Compound 1

| Cells | Concentration (nM) | Average | ±S.D. |
|---|---|---|---|
| Ao-SMCs | 0 | N.D. (0.3 nM or less) | — |
| Ao-SMCs | 100 | 50.6* | 0.167 |
| Ao-SMCs | 1000 | 105.4* | 3.655 |

*P < 0.05

The invention claimed is:
1. A drug-eluting stent graft comprising:
(a) a drug;
(b) a drug-retaining agent; and
(c) a stent graft;

wherein the drug (a) comprises (E)-[5-[2-[1-phenyl-1-(3-pyridyl)methylidenaminoxy]ethyl]-7,8-dihydronaphthalen-1-yloxy]acetic acid or a salt thereof;

wherein the drug-retaining agent (b) is at least one selected from the group consisting of fibrin, gelatin, collagen and hyaluronic acid;

wherein the stent graft (c) is an artificial blood vessel used for intravascular surgery;

wherein the stent graft (c) has a structure in which a metal wire mesh tube is coated inside and/or outside thereof with a resin;

wherein the resin is in the form of fabric which has a thickness in the range of 10 to 160 µm;

wherein a mixture containing the drug (a) and the drug-retaining agent (b) is coated on the outside (the side that contacts the intra-arterial wall) of the stent graft (c); and wherein the drug (a) promotes fixation of the stent graft (c) to an aorta wall.

2. The drug-eluting stent graft according to claim 1, wherein the drug (a) is a slow-release formulation.

3. The drug-eluting stent graft according to claim 2, wherein the slow-release formulation further comprises a biodegradable polymer.

4. The drug-eluting stent graft according to claim 1, wherein the drug (a) is a microsphere formulation.

5. The drug-eluting stent graft according to claim 3, wherein the slow-release formulation is a microsphere formulation.

6. The drug-eluting stent graft according to claim 3, wherein the biodegradable polymer is at least one selected from the group consisting of polylactic acid, polyglycolic acid, a lactic acid-glycolic acid copolymer, and a mixture thereof.

7. The drug-eluting stent graft according to claim 5, wherein the biodegradable polymer is at least one selected from the group consisting of polylactic acid, polyglycolic acid, a lactic acid-glycolic acid copolymer, and a mixture thereof.

8. The drug-eluting stent graft according to claim 5, wherein the biodegradable polymer has a weight average molecular weight of 6,000 to 50,000.

9. The drug-eluting stent graft according to claim 5, wherein the microsphere formulation contains (E)-[5-[2-[1-phenyl-1-(3-pyridyl)methylidenaminoxy]ethyl]-7,8-dihydronaphthalen-1-yloxy]acetic acid or a salt thereof at 5 to 30% by weight.

10. The drug-eluting stent graft according to claim 5, wherein the microsphere formulation has an average particle diameter of 15 to 50 µm.

11. The drug-eluting stent graft according to claim 1, wherein the drug-retaining agent (b) is at least one selected from the group consisting of fibrin, atelocollagen and gelatin.

12. The drug-eluting stent graft according to claim 1, wherein the stent graft (c) includes a mixture comprising gelatin and a micro sphere formulation containing (E)-[5-[2-[1-phenyl-1-(3-pyridyl)methylidenaminoxy]ethyl]-7,8-dihydronaphthalen-1-yloxy]acetic acid, the mixture being applied on an outside of the stent graft.

13. The drug-eluting stent graft according to claim 1, which is used to be placed at an aneurysmal portion in a mammal.

14. The drug-eluting stent graft according to claim 1, which is used to prevent a stent graft-related complication.

15. The drug-eluting stent graft according to claim 14, wherein the stent graft-related complication is migration and/or endoleak.

16. The drug-eluting stent graft according to claim 1, wherein the stent graft (c) is an artificial blood vessel used for aneurysm surgery.

17. The drug-eluting stent graft according to claim 1, wherein the resin is in the form of fabric which has a thickness in the range of 20 to 95 µm.

* * * * *